United States Patent
Alarcon et al.

(10) Patent No.: US 9,947,207 B2
(45) Date of Patent: Apr. 17, 2018

(54) METHOD AND APPARATUS FOR DETECTING AN OBSTRUCTED VIEW

(71) Applicants: GM GLOBAL TECHNOLOGY OPERATIONS LLC, Detroit, MI (US); Christian Kuss, Witney (GB); Tomer Noyhouzer, Montreal (CA); Janine Mauzeroll, Montreal (CA)

(72) Inventors: Michael D. Alarcon, Markham (CA); Christian Kuss, Witney (GB); Tomer Noyhouzer, Montreal (CA); Janine Mauzeroll, Montreal (CA)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 0 days.

(21) Appl. No.: 15/258,205

(22) Filed: Sep. 7, 2016

(65) Prior Publication Data
US 2018/0068552 A1    Mar. 8, 2018

(51) Int. Cl.
*G08B 21/18*    (2006.01)
*B60K 35/00*    (2006.01)
*B60S 1/02*    (2006.01)
*B60S 1/54*    (2006.01)

(52) U.S. Cl.
CPC .......... *G08B 21/182* (2013.01); *B60K 35/00* (2013.01); *B60S 1/026* (2013.01); *B60S 1/54* (2013.01); *B60K 2350/965* (2013.01)

(58) Field of Classification Search
CPC .......... B60H 1/00785; B60K 35/00; B60K 2350/965; B60R 1/00; B60R 1/088; B60R 1/12; B60R 2300/8093; B60S 1/026; B60S 1/08; B60S 1/0822; B60S 1/54; G01S 2007/4039; G02B 27/01; G08B 21/182; H01L 41/081; Y10S 369/908
USPC ........................................... 340/438
See application file for complete search history.

(56) References Cited

U.S. PATENT DOCUMENTS

| | | | | |
|---|---|---|---|---|
| 3,523,244 A | * | 8/1970 | Chleck | G01N 27/225 324/689 |
| 4,994,286 A | * | 2/1991 | Greer | A23N 17/00 426/231 |
| 5,057,754 A | * | 10/1991 | Bell | B60R 16/0231 15/250.001 |
| 5,402,075 A | * | 3/1995 | Lu | G01R 1/07 324/664 |

(Continued)

OTHER PUBLICATIONS

National Semiconductor, Microcontrollers Databook, 1988, pp. i to xvii, 1-1 to 1-7, 1-135 to 1-160.*

(Continued)

*Primary Examiner* — Quan-Zhen Wang
*Assistant Examiner* — Stephen Burgdorf

(57) ABSTRACT

A method and apparatus for detecting an obstructed surface are provided. The apparatus includes: at least one memory comprising computer executable instructions; and at least one processor configured to read and execute the computer executable instructions. The computer executable instructions cause the at least one processor to: detect a current draw from a generator; determine that a surface including a conductive coating is obstructed in response to the current draw being greater than a predetermined threshold; and output a signal to perform a function in response to determining that the surface is obstructed.

10 Claims, 7 Drawing Sheets

(56) References Cited

U.S. PATENT DOCUMENTS

| | | | | |
|---|---|---|---|---|
| 5,459,533 | A | * | 10/1995 | McCooeye ............ G02C 11/08 351/41 |
| 5,748,092 | A | * | 5/1998 | Arsenault ............... G01M 3/18 340/602 |
| 2003/0067447 | A1 | * | 4/2003 | Geaghan ............... G06F 3/0416 345/173 |
| 2006/0202044 | A1 | * | 9/2006 | Ruttiger ............. B60H 1/00785 236/44 C |
| 2009/0092875 | A1 | * | 4/2009 | Daimon .............. H01M 4/9016 429/479 |
| 2009/0212642 | A1 | * | 8/2009 | Krah ..................... G06F 1/3203 307/109 |
| 2013/0095039 | A1 | * | 4/2013 | Lu ....................... A61K 49/0002 424/9.1 |
| 2014/0138131 | A1 | * | 5/2014 | Hao ........................ G06F 3/044 174/257 |
| 2016/0108256 | A1 | * | 4/2016 | Yang ........................ C09D 5/24 428/220 |

OTHER PUBLICATIONS

Texas Instruments, CD405×B Sngle 8-Channel Analog Multiplexer/Demultiplexer with Logic-Level Conversion, Aug. 1998, revised Apr. 2015, pp. 1-38.*

* cited by examiner

METHOD AND APPARATUS FOR DETECTING AN OBSTRUCTED VIEW

Apparatuses and methods consistent with exemplary embodiments relate to obstruction detection. More particularly, apparatuses and methods consistent with exemplary embodiments relate to obstruction detection on surfaces of vehicles.

SUMMARY

One or more exemplary embodiments provide a method and an apparatus that detect obstructions on clear surfaces. More particularly, one or more exemplary embodiments provide a method and an apparatus that detect obstructions on clear surfaces and perform a function to address the detected obstruction.

According to an aspect of an exemplary embodiment, an apparatus for detecting an obstruction is provided. The apparatus includes: a surface comprising a conductive coating: a generator configured to apply a square wave signal to the surface; and a controller configured to detect a current draw from the generator, determine that the surface is obstructed in response to the current draw being greater than a predetermined threshold, and output a signal in response to determining that the surface is obstructed.

The conductive coating may include a nanoparticle coating.

The conductive coating may include at least one from among metallic nanoparticles, Fluorine doped Tin Oxide (FTO), Indium Tin Oxide (ITO), conductive ink, and carbon nanotubes (CNT).

The surface may include at least one from among a sensor surface, a windshield, a lens, a rear vehicle window, a vehicle window, a camera lens, a side view mirror, a clear surface, a reflective surface and a rear view mirror.

The controller may be configured to output the signal to control at least one from among: a display to output a notification that the surface is obstructed, a speaker to output an audible notification that the surface is obstructed, a defroster to defrost the surface, a defogger to defog the surface, and a cleaning device to clean the obstructed surface.

The square wave signal may include a four volt square wave signal.

According to an aspect of an exemplary embodiment, an apparatus for detecting an obstruction is provided. The apparatus includes: at least one memory comprising computer executable instructions; and at least one processor configured to read and execute the computer executable instructions, the computer executable instructions causing the at least one processor to: detect a current draw of a generator; determine that a surface is obstructed in response to the current draw being greater than a predetermined threshold; and output a signal to perform a function in response to determining that the surface is obstructed.

The surface may include a conductive coating.

The conductive coating may include at least one from among metallic nanoparticles, Fluorine doped Tin Oxide (FTO), Indium Tin Oxide (ITO), conductive ink, and carbon nanotubes (CNT).

The surface may include at least one from among a windshield, a lens, a sensor surface, a rear vehicle window, a vehicle window, a camera lens, a side view mirror, a clear surface, a reflective surface and a rear view mirror.

The function may include at least one from among: outputting a display notification that the surface is obstructed, outputting an audible notification that the surface is obstructed, defrosting the surface, defogging the surface, and cleaning the obstructed surface.

The square wave signal may include a four volt square wave signal.

According to an aspect of an exemplary embodiment, a method for detecting an obstruction is provided. The method includes: detecting a current draw based on a signal output by a generator; determining that a surface including a conductive coating is obstructed in response to the current draw being greater than a predetermined threshold; and controlling to perform a function in response to determining that the surface is obstructed.

The conductive coating may include a nanoparticle coating.

The conductive coating may include at least one from among metallic nanoparticles, Fluorine doped Tin Oxide (FTO), Indium Tin Oxide (ITO), conductive ink, and carbon nanotubes (CNT).

The surface may include at least one from among a windshield, a lens, a sensor surface, a rear vehicle window, a vehicle window, a camera lens, a side view mirror, a clear surface, a reflective surface and a rear view mirror.

The controlling to perform the function may include controlling to perform at least one from among: output a display notification that the surface is obstructed, output an audible notification that the surface is obstructed, control a defogger to defog the surface, and control a cleaning device to clean the obstructed surface.

The signal may include a four volt square wave signal.

The method may further include generating the signal and providing the generated signal to the surface.

According to an aspect of an exemplary embodiment, non-transitory computer readable medium comprising computer executable instructions executable by a processor to perform the method for detecting the obstruction is provided.

Other objects, advantages and novel features of the exemplary embodiments will become more apparent from the following detailed description of exemplary embodiments and the accompanying drawings.

DETAILED DESCRIPTION

Figure 1:
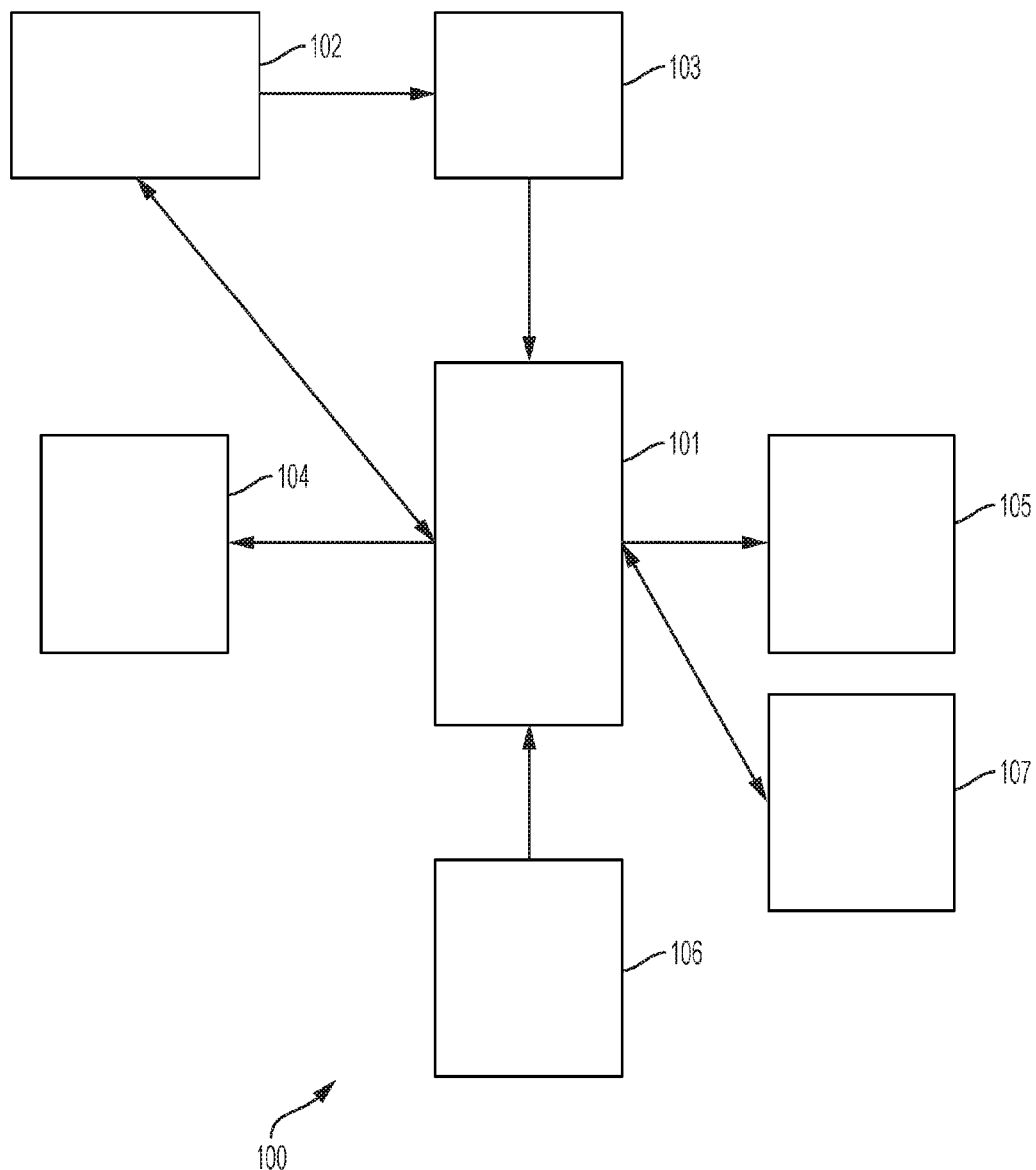
FIG. 1 shows a block diagram of an apparatus for detecting an obstruction according to an aspect of an exemplary embodiment.

An apparatus and method that detect obstruction will now be described in detail with reference to FIGS. 1-6 of the accompanying drawings in which like reference numerals refer to like elements throughout.

The following disclosure will enable one skilled in the art to practice the inventive concept. However, the exemplary embodiments disclosed herein are merely exemplary and do not limit the inventive concept to exemplary embodiments described herein. Moreover, descriptions of features or aspects of each exemplary embodiment should typically be considered as available for aspects of other exemplary embodiments.

It is also understood that where it is stated herein that a first element is "connected to," "formed on," or "disposed on" a second element, the first element may be connected directly to, formed directly on or disposed directly on the second element or there may be intervening elements between the first element and the second element, unless it is stated that a first element is "directly" connected to, formed on, or disposed on the second element. In addition, if a first element is configured to "send" or "receive" information from a second element, the first element may send or receive the information directly from the second element, send or receive the information via a bus, receive the information via a network, or send or receive the information via intermediate elements, unless the first element is indicated to receive information "directly" from the second element.

Throughout the disclosure, one or more of the elements disclosed may be combined into a single device or combined into one or more devices. In addition, individual elements may be provided on separate devices.

Surfaces may become obstructed if dirt, dust, humidity, moisture, or another substance is deposited on the surface. Surfaces may include clear surfaces such as windshields and camera lenses, and reflective surfaces such as mirrors. When clear and reflective surfaces become obstructed, it may impair the ability to see through a clear surface and the ability to see a reflection on a reflective surface. Thus, prevention, detection, and clearing of obstructed surfaces may address the impairment to the ability to see through a clear surface and the ability to see a reflection on a reflective surface.

FIG. 1 shows a block diagram of an apparatus for detecting obstruction 100 according to an aspect of an exemplary embodiment. As shown in FIG. 1, the apparatus for detecting obstruction 100, according to an exemplary embodiment, includes a controller 101, a signal generator 102, a conductive surface 103, an output 104, a surface clearing device 105, a user input 106 and a storage 107. However, the apparatus for detecting obstruction 100 is not limited to the aforementioned configuration and may be configured to include additional elements and/or omit one or more of the aforementioned elements.

The controller 101 controls the overall operation and function of the apparatus for detecting obstruction 100. The controller 101 may control one or more of a signal generator 102, a conductive surface 103, an output 104, a surface clearing device 105, a user input 106 and a storage 107 of the apparatus for detecting obstruction 100. The controller 101 may include one or more from among a processor, a microprocessor, a central processing unit (CPU), a graphics processor, Application Specific Integrated Circuits (ASICs), Field-Programmable Gate Arrays (FPGAs), state machines, circuitry and a combination of hardware, software and firmware components.

The controller 101 is configured to send and/or receive information from one or more of a signal generator 102, a conductive surface 103, an output 104, a surface clearing device 105, a user input 106 and a storage 107 of the apparatus for detecting obstruction 100. The information may be sent and received via a bus or network, or may be directly read or written to/from one or more of a signal generator 102, a conductive surface 103, an output 104, a surface clearing device 105, a user input 106 and a storage 107 of the apparatus for detecting obstruction 100.

The signal generator 102 is configured to generate a signal that is output on the conductive surface 103. The signal may be a periodic signal. The periodic signal may be a square wave signal or a pulse width modulated signal. The signal may also be a 4V signal. Moreover, the current draw of the signal generator 102 may be detected by the controller 101.

The conductive surface 103 is configured to receive the signal from the signal generator 102. Moreover, the conductive surface 103 may be disposed on, integrated with or combined with a surface on which obstruction detection is desired. For example, the surface may be a clear surface such as a windshield, a lens, a rear vehicle window, a vehicle window, a camera lens, a side view mirror, a rear view mirror, etc.

The conductive surface 103 may be a coating, a lattice, conductive ink, etc. The conductive surface may comprise nanoparticles. The conductive surface 103 may comprise one or more from among Fluorine doped Tin Oxide (FTO), which is an electrically conductive transparent ceramic, Indium Tin Oxide (ITO), conductive ink (e.g., PEDOT: PSS), metallic nanoparticles, Pt-NPs, and carbon nanotubes (CNT). For example, FTO may be applied as a thin film layer onto surfaces such as glass and flexible organic polymers (e.g., plastic). According to an example, FTO may be coated onto polymer plastic sheet.

According to an example, the conductive surface 103 may comprise silver particles. For example, silver nanoparticles may be deposited on the conductive surface 103 from a silver nitrate solution using a two-step electrochemistry pulse method. The method may create a unified coverage of flower like structures with a maximum size of 3 μm.

The conductive surface 103 may react with a substance disposed on a surface of the conductive surface 103 or on a clear or reflective surface on which the conductive surface is disposed. The reaction with the substance may increase the current draw of the conductive surface 103. The increase in current draw may be detected by the controller 101. Based on the increase in current draw, the controller 101 may detect an obstruction on the conductive surface and control the output 104 to perform a function based on the detected obstruction.

The output 104 outputs information in one or more forms including: visual, audible and/or haptic form. The output 104 may be controlled by the controller 101 to provide outputs to the user of the apparatus for detecting obstruction 100. The output 104 may include one or more from among a speaker, a centrally-located a display, a head up display, a windshield display, a haptic feedback device, a vibration device, a tactile feedback device, a tap-feedback device, a holographic display, an instrument light, an indicator light, etc.

The output 104 may output a notification including one or more from among an audible notification, a light notification, and a display notification. The notification may include information about an obstructed surface and/or instructions on how to clear the obstructed surface. For example, a displayed notification may include one or more selectable display elements that initiate a surface clearing device 105 such as a cleaning device, defrosting device or a defogging device.

The surface clearing device 105 is configured to clear an obstructed surface. The surface clearing device may include one or more form among a spraying device, a wiper device, a defogging device, a defrosting device, etc. The spraying device may be configured to spray a fluid such as water, wiper fluid, or a cleanser on the obstructed surface to clean a substance causing the obstruction. The wiper device may be configured to move or slide a wiper or a blade across the obstructed surface to remove a substance causing the obstruction. The defogging device may be configured to direct a jet of air onto a surface to remove the condensation causing the obstruction of the surface. The defrosting device may be configured to heat the surface to melt the ice or snow causing the obstruction of the surface.

The user input 106 is configured to provide information and commands to the apparatus for detecting obstruction 100. The user input 106 may be used to provide user inputs, commands, etc., to the controller 101. The user input 106 may include one or more from among a touchscreen, a keyboard, a soft keypad, a button, a motion detector, a voice input detector, a microphone, a camera, a trackpad, a mouse, a touchpad, etc. The user input 106 may be configured to receive a user input to acknowledge or dismiss the notification output by the output 104. The user input 106 may also be configured to receive a user input to cycle through notifications, different screens of a notification, or to select a display element that initiates a surface clearing device 105.

The storage 107 is configured for storing information and retrieving information used by the apparatus for detecting obstruction 100. The storage 107 may be controlled by the controller 101 to store and retrieve obstruction information including one or more from among a name of an obstructed surface, a type of obstructed surface, a type of obstruction, and a type of clearing device used to clear the obstruction, etc. The obstruction information may be used by the controller 101 to control the appropriate surface clearing device 105. Moreover, the obstruction information may be used by the controller 101 to control the output 104 to output the appropriate information or notification. The storage 107 may also include the computer instructions configured to be executed by a processor to perform the functions of the apparatus for detecting obstruction 100.

The storage 107 may include one or more from among floppy diskettes, optical disks, CD-ROMs (Compact Disc-Read Only Memories), magneto-optical disks, ROMs (Read Only Memories), RAMs (Random Access Memories), EPROMs (Erasable Programmable Read Only Memories), EEPROMs (Electrically Erasable Programmable Read Only Memories), magnetic or optical cards, flash memory, cache memory, and other type of media/machine-readable medium suitable for storing machine-executable instructions.

According to an exemplary embodiment, the controller 101 of the apparatus for detecting obstruction 100 is configured to detect a current draw from the generator, determine that the surface is obstructed in response to the current draw being greater than a predetermined threshold, and output a signal in response to determining that the surface is obstructed.

According to an exemplary embodiment, the controller 101 of the apparatus for detecting obstruction 100 is configured to detect a current draw of a generator; determine that a surface is obstructed in response to the current draw being greater than a predetermined threshold; and output a signal to perform a function in response to determining that the surface is obstructed.

The controller 101 may be configured to output the signal to control at least one from among: a display to output a notification that the surface is obstructed, a speaker to output an audible notification that the surface is obstructed, a defroster to defrost the surface, a defogger to defog the surface, and a cleaning device to clean the obstructed surface.

According to another exemplary embodiment, the controller 101 of the apparatus for detecting obstruction 100 may be configured to control the output 104 to output a signal to display a notification that the surface is obstructed, to output an audible notification that the surface is obstructed. The controller 101 of the apparatus for detecting obstruction 100 may also output a signal to initiate the surface clearing device 105 to clear the obstructed surface.

Figure 2:
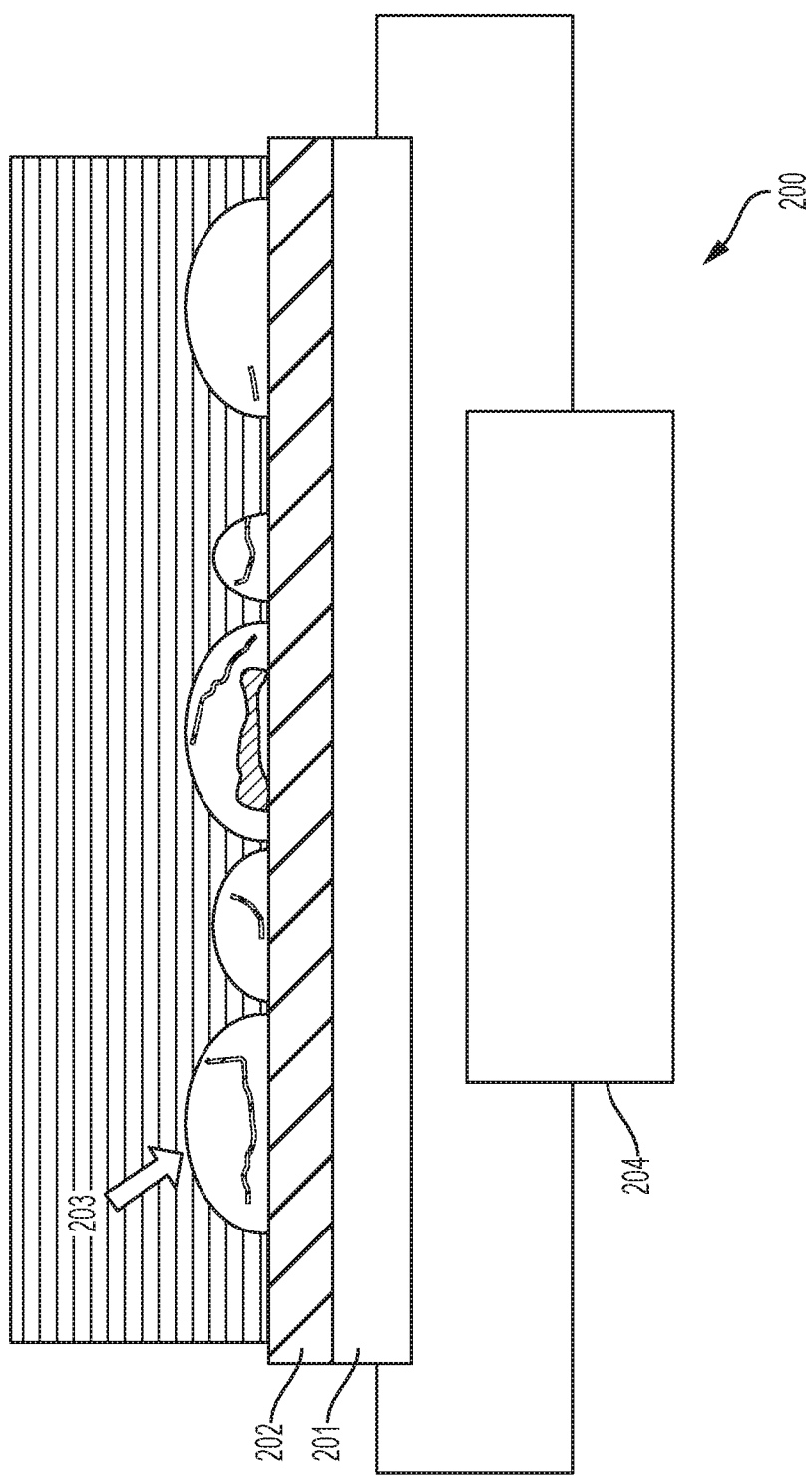
FIG. 2 shows a diagram of an apparatus for detecting an obstruction according to an aspect of an exemplary embodiment.

FIG. 2 shows a diagram of an apparatus for detecting obstruction 200 according to an aspect of an exemplary embodiment. As shown in FIG. 2, a generator 204 generates a square wave signal, which is pass through a surface 201, for example, a glass surface or a glass substrate. A coating 202, e.g., a conductive coating, a nanoparticle coating, a silver nanoparticle coating, etc., is disposed on the surface 201. Obstructing substances 203 that are deposited on the surface 202 affect the current draw from the generator 204. The effect on the current draw can be detected and used to determine whether the surface is obstructed.

The current draw may be detected using a potentiostat, which allows an application of a defined voltage-time function to the conductive surface 103, while quantifying the current that flows through the conductive surface 103. Obstruction of the conductive surface is detected by recording a video of a test image with the test surface between image and camera. The recorded test image is compared to a benchmark test image taken through an unobstructed surface. The comparison is quantified by calculating the two dimensional (2D) correlation coefficient between the recorded test frame and the benchmark image. The 2D correlation coefficient indicates an amount of obstruction on the conductive surface 103. For example, a coefficient of 1 indicates an unobstructed image and a coefficient of 0 indicates a completely obstructed image. By quantifying the current that flows through the conductive surface 103 and the corresponding 2D correlation coefficient, it may be determined which quantity or level of current flow indicates a dirty or obstructed conductive surface.

The surface 201 may be one or more from among a glass substrate, a windshield, a lens, a rear vehicle window, a vehicle window, a camera lens, a side view mirror, and a rear view mirror. The coating 202 may include one or more from among conductive elements, nanoparticles, silver nanoparticles, etc. The square wave signal may be a four volt square wave signal.

Figure 3A:
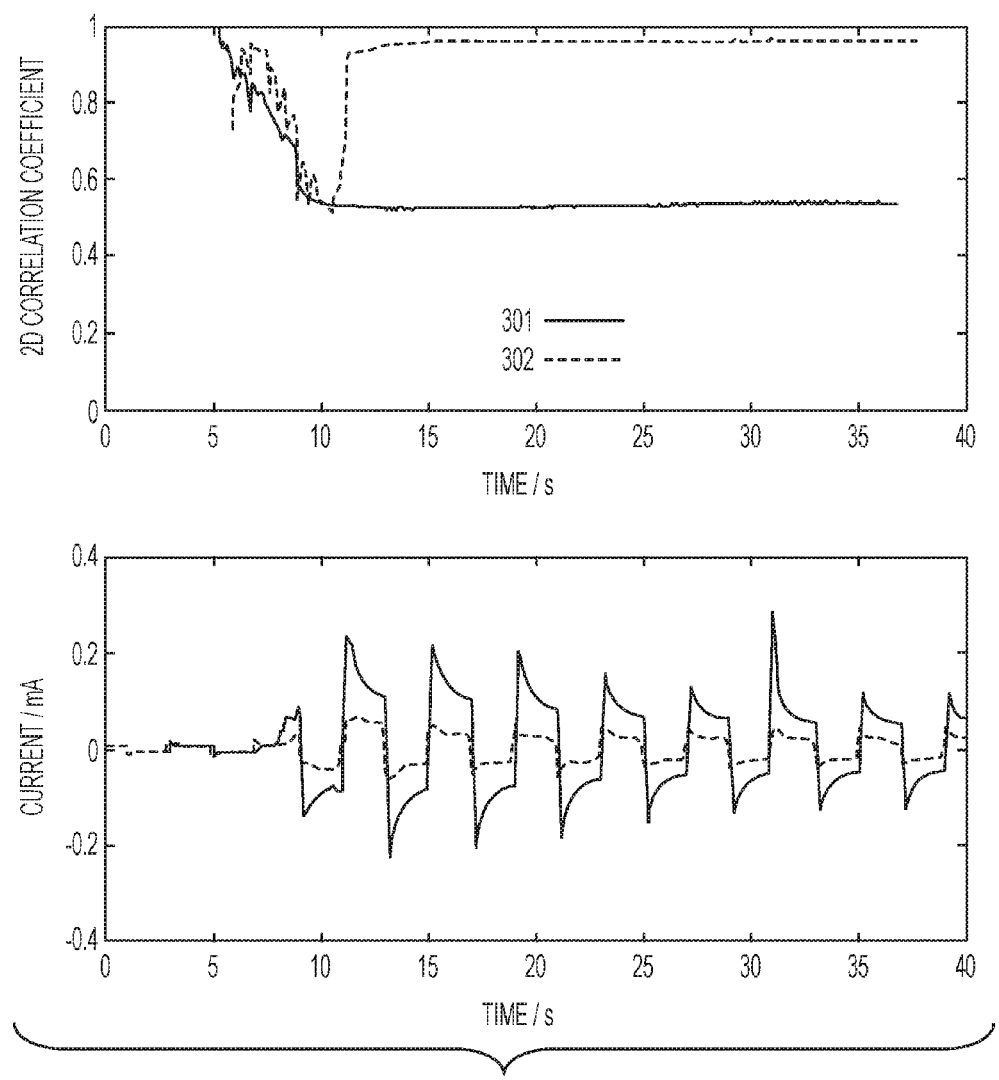
FIGS. 3A and 3B are graphs illustrating a two-dimensional (2D) correlation coefficient as a function of time and a current draw as a function of time, respectively, to illustrate an obstruction detection method for dirt spray and water spray according to an aspect of an exemplary embodiment.
Figure 3B:
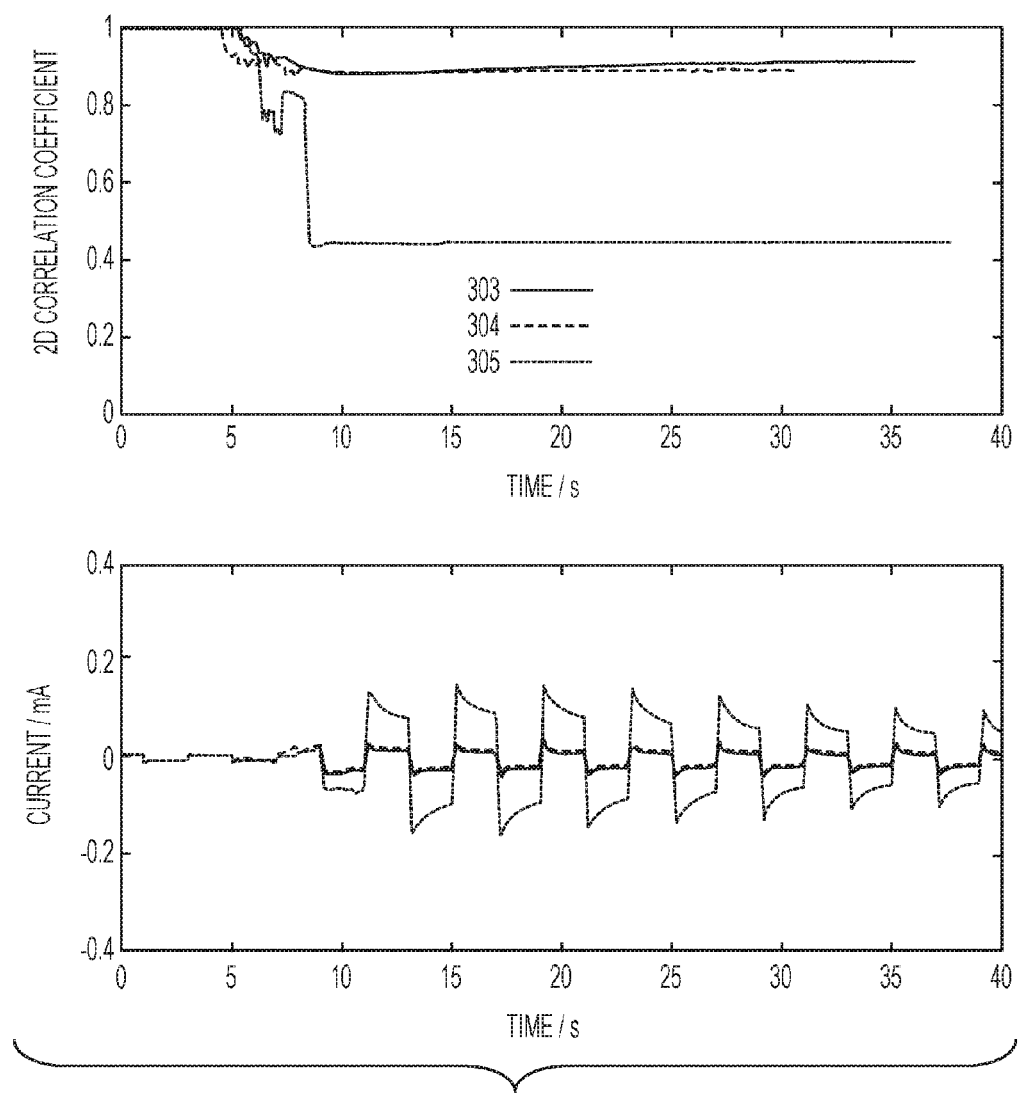

FIGS. 3A and 3B are graphs illustrating a two-dimensional (2D) correlation coefficient as a function of time and a current draw as a function of time, to illustrate an obstruction detection method for dirt spray and water spray according to an aspect of an exemplary embodiment.

Referring to FIG. 3A, lines representing 2D correlation coefficients and lines representing a current draw in mA are graphed. The lines represent: dirt spray on Fluorine doped Tin Oxide (FTO) 301; and dirt spray on FTO with Ag-NP 302. The 2D correlation coefficient is measured to quantify the amount of obstruction on the surface. As shown, the current draw increases as the 2-D correlation decreases, which indicates that the current draw increases as the surface gets more obstructed or that the current draw is inversely proportional to the 2-D correlation coefficient. By observing both figures, the current draw is proportional to the obstruction amount where 301 has a much higher current draw since it is more obstructed and 302 has less current draw since it is less obstructed.

Referring to FIG. 3B, lines representing 2D correlation coefficients and lines representing a current draw in mA are graphed. The lines represent: water spray on FTO 303; water spray on FTO 304; and water spray on FTO with Ag-NP 305. As shown, the current draw increases as the 2-D correlation decreases, which indicates that the current draw increases as the surface gets more obstructed or that the current draw is inversely proportional to the 2-D correlation coefficient. By observing both figures, the current draw is proportional to the obstruction amount where 305 has a much higher current draw since it is more obstructed and 303 and 304 have less current draw since it is less obstructed.

Figure 4:
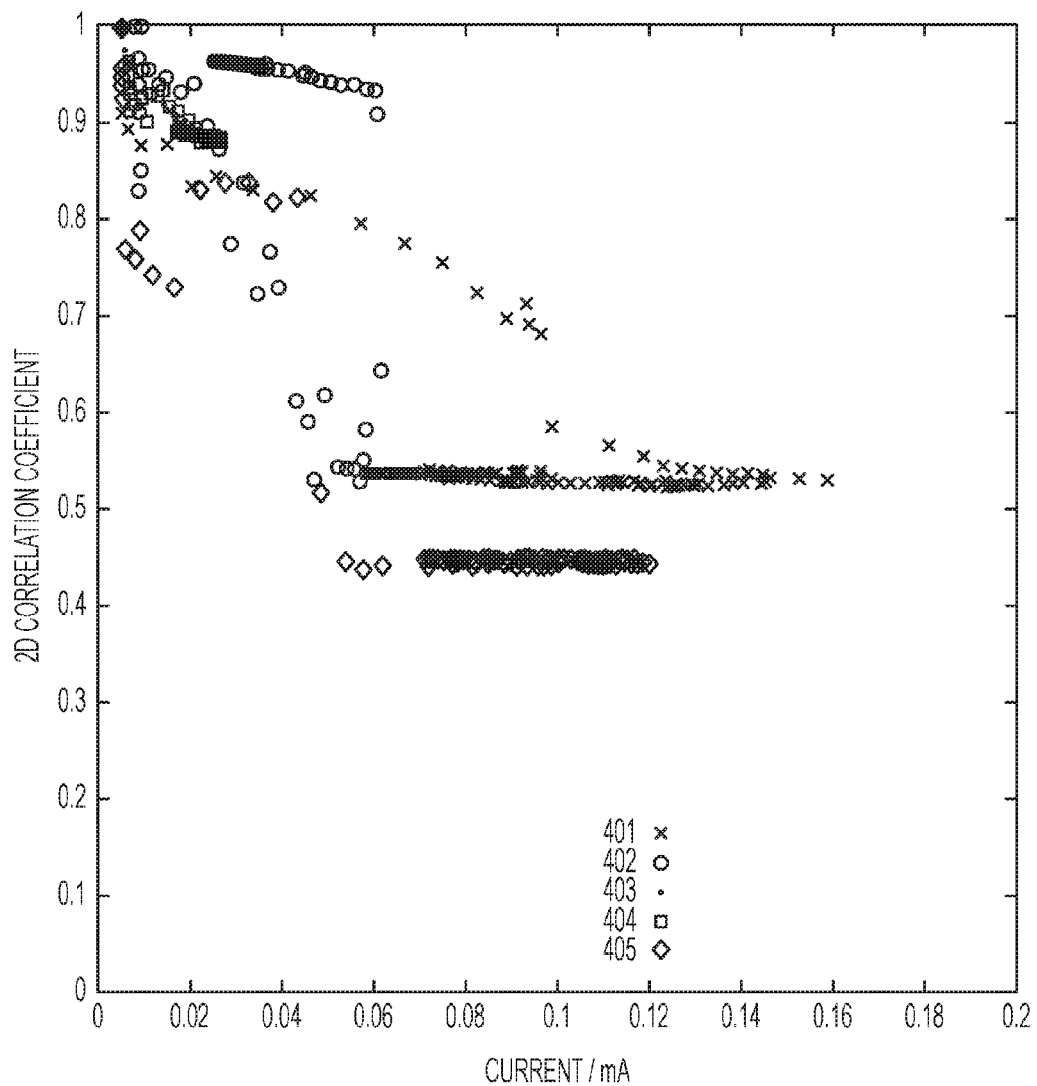
FIG. 4 shows a scatter plot with data points scattered according to a two-dimensional (2D) correlation coefficient and corresponding current draw according to an aspect of an exemplary embodiment.

FIG. 4 shows a scatter plot with data points scattered according to a two-dimensional (2D) correlation coefficient and corresponding current draw according to an aspect of an exemplary embodiment. The points on the scatter plot represent: dirt spray, FTO, 4V square wave 401; dirt spray, FTO Ag-NP, 4V square wave 402; water spray; 4V square wave 1 403; water spray, 4V square wave 2 404; and water spray, FTO Ag-NP, 4V square wave 405. As can be determined from the scatter plot, the 2D correlation coefficient decreases as the current draw (milliamps (mA)) increases.

Figure 5:
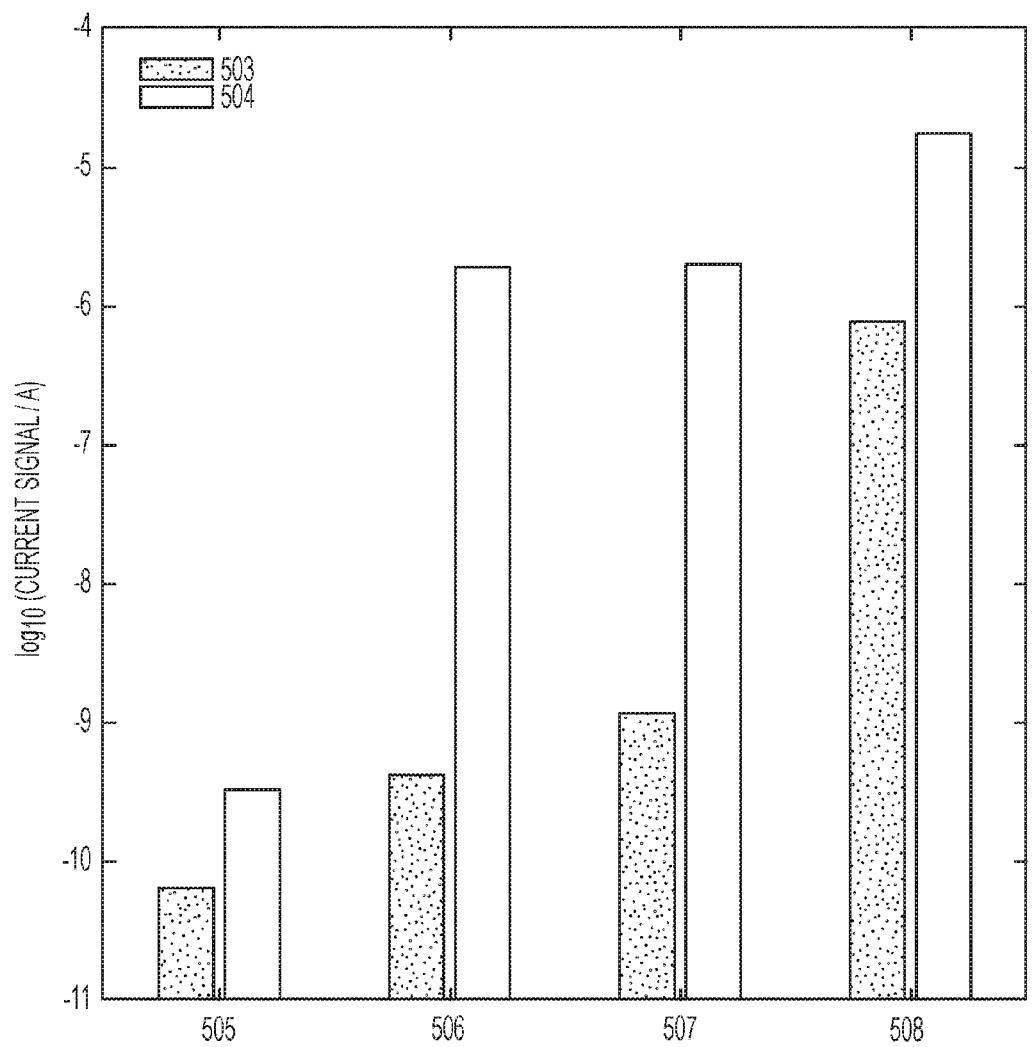
FIG. 5 is a graph illustrating a current draw as a function of time to illustrate an obstruction detection method for dried clay according to an aspect of an exemplary embodiment.

FIG. 5 is a graph illustrating a current draw as a function of time to illustrate an obstruction detection method for dried clay according to an aspect of an exemplary embodiment. Referring to FIG. 5, the $\log_{10}$ of the current signal in Amperes is greater for a dirty surface 504 than it is for a clean surface 503. This holds true for dried conditions 505, cold humid conditions 506, cold sea humid conditions 507, and hot humid conditions 508.

Figure 6:
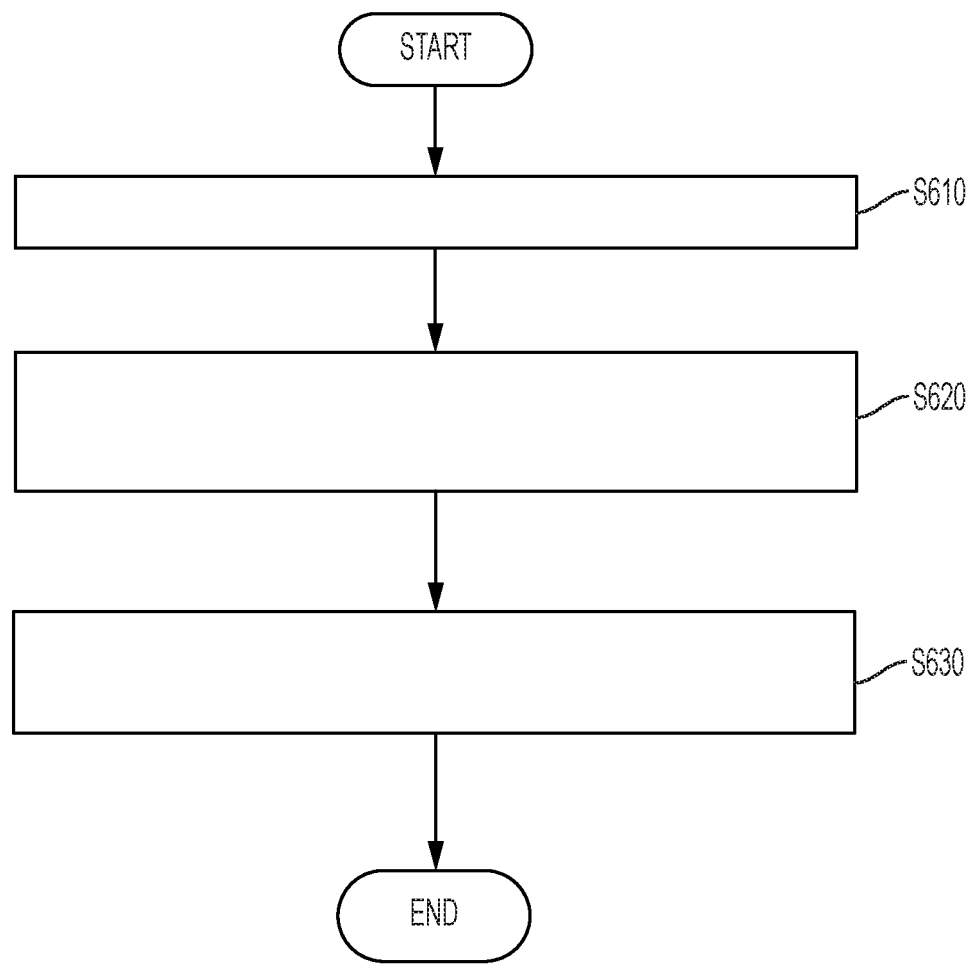
FIG. 6 illustrates a flowchart for a method of detecting an obstruction according to an aspect of an exemplary embodiment.

FIG. 6 shows a flowchart for a method for detecting an obstruction according to an aspect of an exemplary embodiment. The method of FIG. 6 may be performed by the apparatus for detecting obstruction 100 or may be encoded into a computer readable medium as instructions that are executable by a computer to perform the method.

Referring to FIG. 6, the current draw of a generator is detected in operation S610. For example, the current draw may be detected based on a signal output by a generator. It is then determined that a surface is obstructed in response to the current draw being greater than a predetermined threshold or in response to an increase in the current draw in operation S620. For example, if the increase in the current draw is greater than a predetermined threshold, it may be determined that the surface is obstructed. A signal to perform a function is then output in operation S630 in response to determining that the surface is obstructed. For example, the signal may control to perform a function including at least one from among displaying a notification that the surface is obstructed, outputting an audible notification that the surface is obstructed, defrosting the surface, defogging the surface, and cleaning the obstructed surface, in operation S630.

The processes, methods, or algorithms disclosed herein can be deliverable to/implemented by a processing device, controller, or computer, which can include any existing programmable electronic control device or dedicated electronic control device. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

One or more exemplary embodiments have been described above with reference to the drawings. The exemplary embodiments described above should be considered in a descriptive sense only and not for purposes of limitation. Moreover, the exemplary embodiments may be modified without departing from the spirit and scope of the inventive concept, which is defined by the following claims.

What is claimed is:

1. An apparatus for detecting an obstruction, the apparatus comprising:
   a surface comprising a conductive coating;
   a generator configured to apply a four volt square wave signal to the surface; and
   a controller configured to detect a current draw from the generator, determine that the surface is obstructed in response to the current draw being greater than a predetermined threshold, and output a signal in response to determining that the surface is obstructed,
   wherein the surface comprises at least one from among a sensor surface, a camera lens, and a reflective surface,
   wherein the controller is configured to output the signal to control at least one from among: a display to output a notification that the surface is obstructed, a speaker to output an audible notification that the surface is obstructed, and a cleaning device to clean the obstructed surface, and
   wherein the conductive coating comprises a nanoparticle coating comprising flower like structures with a maximum size of 3 μm.

2. The apparatus of claim 1, wherein the controller is further configured to determine a level of obstruction based on the detected current draw.

3. The apparatus of claim 2, wherein the controller is further configured to perform a function according to the level of obstruction.

4. An apparatus for detecting an obstruction, the apparatus comprising:
   at least one memory comprising computer executable instructions; and
   at least one processor configured to read and execute the computer executable instructions, the computer executable instructions causing the at least one processor to:
   detect a current draw of a generator outputting a four volt square wave signal being applied to a surface;
   determine that the surface is obstructed in response to the current draw being greater than a predetermined threshold; and
   output a signal to perform a function in response to determining that the surface is obstructed, wherein the surface comprises at least one from among a sensor surface, a camera lens, and a reflective surface, wherein the function comprises at least one from among: outputting a display notification that the surface is obstructed, outputting an audible notification that the surface is obstructed, and cleaning the obstructed surface, and wherein the surface comprises a nanoparticle coating comprising flower like structures with a maximum size of 3 μm.

5. The apparatus of claim 4, wherein the computer executable instructions further cause the at least one processor to determine a level of obstruction based on the detected current draw.

6. The apparatus of claim 5, wherein the computer executable instructions further cause the at least one processor to control to perform the function according to the level of obstruction.

7. A method for detecting obstruction, the method comprising detecting a current draw of a surface based on a four volt square wave signal output by a generator;

determining that the surface including a conductive coating is obstructed in response to the current draw being greater than a predetermined threshold; and controlling to perform a function in response to determining that the surface is obstructed, wherein the surface comprises at least one from among a sensor surface, a camera lens, and a reflective surface, wherein the controlling to perform the function comprises controlling to perform at least one from among: output a display notification that the surface is obstructed, output an audible notification that the surface is obstructed, and control a cleaning device to clean the obstructed surface, and wherein the conductive coating comprises a nanoparticle coating comprising flower like structures with a maximum size of 3 μm.

8. A non-transitory computer readable medium comprising computer executable instructions executable by a processor to perform the method of claim 7.

9. The method of claim 7, further comprising determining a level of obstruction based on the detected current draw.

10. The apparatus of claim 9, wherein the controlling to perform the function is performed according to the level of obstruction.

* * * * *